United States Patent [19]

David et al.

[11] Patent Number: 4,555,664
[45] Date of Patent: Nov. 26, 1985

[54] PROCESS AND DEVICE FOR INSPECTING A SURFACE IN SIMULATED MANNER WHICH DIFFERS FROM THE REAL SURFACE SCANNING BY AN EDDY CURRENT TRANSDUCER

[75] Inventors: Bernard David, Gif sur Yvette; Michel Pigeon, Bures sur Yvette, both of France

[73] Assignee: Commissariat a l'Energie Atomique, Paris, France

[21] Appl. No.: 413,517

[22] Filed: Aug. 31, 1982

[30] Foreign Application Priority Data

Sep. 14, 1981 [FR] France ................... 81 17312

[51] Int. Cl.[4] ............ G01N 27/72; G01R 33/12
[52] U.S. Cl. ........................ 324/225; 324/234; 324/262
[58] Field of Search ............ 324/219–221, 324/225, 227, 237, 238, 240–242, 262; 343/5 SC; 364/507, 550, 551, 515, 518–521, 731; 73/619; 367/11

[56] References Cited

U.S. PATENT DOCUMENTS 3,419,797 12/1968 Libby .................... 324/220
4,194,149 3/1980 Holt et al. ............... 324/220
4,225,929 9/1980 Ikeda .................... 324/515 X
4,241,412 12/1980 Swain .................... 324/731

FOREIGN PATENT DOCUMENTS 1950122 10/1969 Fed. Rep. of Germany .
2518866 1/1976 Fed. Rep. of Germany .

Primary Examiner—Gerard R. Strecker
Assistant Examiner—Walter E. Snow
Attorney, Agent, or Firm—Kerkam, Stowell, Kondracki and Clarke

[57] ABSTRACT

The invention relates to a process and to devices for the inspection of the surface of a member by means of an eddy current probe. By scanning the member means of the transducer following a given path, the sampled values of the signal supplied by the transducer are recorded for clearly defined positions of the transducer. By restoring the signals, it is possible to simulate a displacement of the transducer along a different path and-/or simulate the displacement of a larger size or different type of transducer. The process may be used in steam generators in nuclear reactors and to the examination of irradiated fuel rods in these reactors.

14 Claims, 10 Drawing Figures

PROCESS AND DEVICE FOR INSPECTING A SURFACE IN SIMULATED MANNER WHICH DIFFERS FROM THE REAL SURFACE SCANNING BY AN EDDY CURRENT TRANSDUCER

BACKGROUND OF THE INVENTION

The present invention relates to a process for the inspection of the surface of a member by means of an eddy current transducer supplying a signal representing the state of said surface, as well as to devices for performing such a process.

It is at present standard practice to inspect the surface of members made from electrically conductive materials by using eddy current transducers. The signal supplied by the transducer gives information on the surface state and the possible presence of defects in the surface. For example, an inspection of this type is carried out periodically in the tubes of heat exchangers or steam generators of nuclear power stations. However, This application is in no way limitative and surface inspections by means of eddy current transducers are carried out in numerous other fields.

Whatever the application, the hitherto used inspection procedure consists of carrying out a maximum complete scan or sweep of the surface to be inspected and observing by means of a direct reading system variations of the signal supplied by the transducer in order to deduce the state of the inspected surface.

Although this inspection procedure has hitherto been used in a standard manner, it has a certain number of disadvantages linked with the need of adapting the transducer and the path followed by it to the size and orientation of the defects. Thus, for easy detection of the defect, the size of the transducer must be as close as possible to that of the defects to be detected. Moreover, when investigating point defects, differential transducers are used, which must be oriented in such a way that the direction linking the two windings forming the same coincide with the axis having the greatest variation gradient of the signal supplied by the transducer. However, there are at least two cases where these conditions cannot be satisfied:

(1) When neither the size nor the orientation of the defects is known.
(2) When the path taken by the transducer is already established.

BRIEF SUMMARY OF THE INVENTION

The present invention relates to a process for the inspection of the surface of a member by means of an eddy current transducer not having the disadvantages of the prior art process and in particular making it possible to perform a simulated displacement of the transducer in the desired direction, which can differ from the real surface scan direction by the transducer, whereby it is possible to simulate the transducer size to the type of defect which it is desired to detect.

The present invention therefore proposes a process for the inspection of the surface of a member by means of an eddy current transducer comprising at least one eddy current probe supplying a signal representing the state of said surface, wherein it comprises using the transducer to scan in a given order elementary measurement zones defined on the surface of the member, recording the sampled values of the signal supplied by the transducer for each of the elementary measurement zones and restoring the signals obtained on the basis of one or more sampled values corresponding to adjacent zones of the surface and in a random order.

According to the invention, it is possible to use either an absolute transducer having at least one probe comprising a first eddy current coil, or a differential transducer comprising at least one probe having two coils.

According to a first embodiment of the process according to the invention, the signals corresponding in each case to one of the recorded sampled values are restored in accordance with an order differing from the scanning order. It is therefore possible to carry out a simulated displacement of the transducer in an optimum direction for the detection of defects. In this case, when the elementary measuring zones define at least two different directions, the scanning order can follow a first direction, whilst the signal restoration order follows a direction differing from that of the first direction.

According to a second embodiment of the process according to the invention, the restoration is by signals, each of which represents the mean value of a group of sampled values corresponding to adjacent zones. The size of the transducer can therefore be increased in a simulated manner, which makes it possible to detect defects, whose large size compared with that of the transducer would not have permitted the latter to detect them.

According to a third embodiment of the process according to the invention, restoration is by signals, whereof each represents the difference between the sampled values corresponding to two adjacent zones. This embodiment, which exclusively relates to the use of an absolute transducer, makes it possible to simulate the type of transducer used by simulating a sweep by means of a differential transducer.

In a variant combining the characteristics of the second and third embodiments of the invention, restoration is by signals, each of which represents the difference between the mean values of two groups of sample values corresponding to adjacent zones. It is therefore possible, by carrying out the scan with a point transducer, to simulate the nature and shape of the transducer in order to obtain signals of the type conventionally supplied by a larger differential transducer.

Obviously the first embodiment can be combined with others in such a way that the simulated scan determined by the restored signals corresponds to the scan which would have been made by a transducer of a different type and/or having different dimensions from that actually used, said simulated scan also being performed in an order differing from the real scan.

The present invention also relates to a device for inspecting the surface of a member by means of an eddy current transducer, comprising at least one eddy current probe supplying a signal representing the state of said surface.

According to a first embodiment this device comprises means for making the said transducer scan in a given order elementary measurement zones defined on the surface of the member, means for storing the sampled values of the error signals supplied by the transducer for each of the elementary zones and means for restoring a series of signals from one or more sampled values corresponding to adjacent zones of the surface in a random desired order.

According to a second embodiment the device comprises means for making the transducer scan in a given order the elementary measurement zones defined on the surface of the member and in at least two different directions, the scanning order following a first of these directions, means for supplying to different channels each of the sampled values of the error signal supplied by the transducer or each of the elementary measurement zones corresponding to said first direction and means for recording on each of these channels, values sampled in accordance with an order corresponding to another direction.

BRIEF DESCRIPTION OF THE DRAWINGS

The invention will be described in greater detail hereinafter relative to non-limitative embodiments and the attached drawings, wherein.

DETAILED DESCRIPTION OF THE PREFERRED EMBODIMENTS

The principle of the inspection process according to the invention will firstly be described with reference to FIGS. 1a, 1b, 2a and 2b, when applied to a parallelepiped 10, whose upper surface 12 is examined by means of an absolute transducer 14 comprising, in the simplest case, an eddy current probe having a single coil whose axis is perpendicular to surface 12.

However, it is pointed out that the process of the invention can be applied to members having widely varying shapes, including more particularly members whose scanning can be carried out by displacing the transducer in a single direction. Among the members of this type, particular reference can be made to solid bars or tubes, which can be inspected by moving an encirclement-type eddy current transducer parallel to the axis thereof. The interior of such tubes can be inspected by means of an appropriate transducer, which is also moved parallel to the tube axis. In both cases the size and type of the equivalent transducer can be modified according to the invention.

Figure 1A:
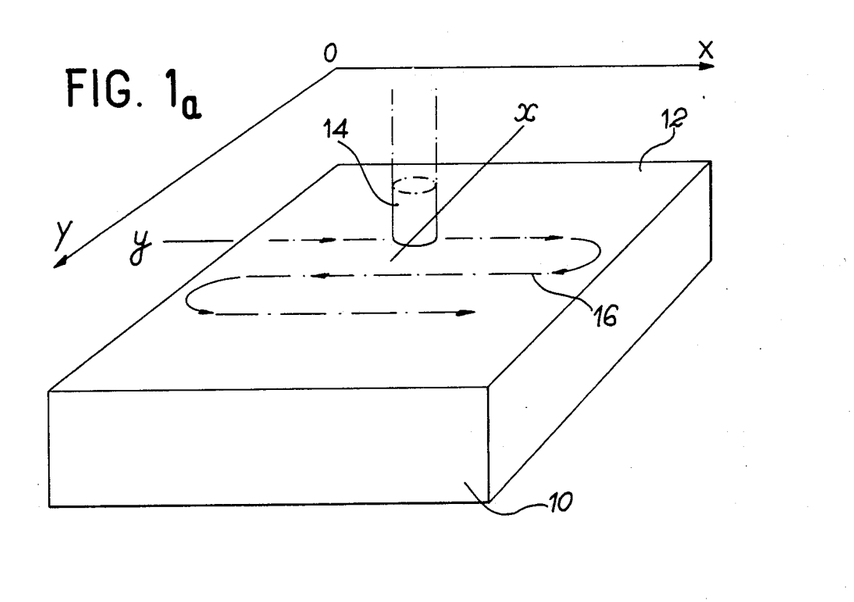
FIG. 1a diagrammatically illustrate the principle on which and 1b the invention is based, FIG. 1a showing an example of the scanning of a planar surface by means of an absolute eddy current transducer and FIG. 1b showing the resulting filling order of a table of the sampled values of the signal supplied by the transducer, the table being drawn up as a function of predetermined coordinates of the examined member.

In the case of a surface, like surface 12 of FIG. 1, it cannot be scanned by moving the transducer in one direction. For this reason, in FIG. 1 the displacements of the transducer 14 parallel to surface 12 are marked by means of two perpendicular coordinates OX and OY. Transducer 14 which, in per se known manner, is associated with appropriate equipment, supplies a voltage signal, whose variations represent the defects of the examined member.

According to the prior art inspection procedures and according to the process of the invention, the dimensions of transducer 10 and of the path taken by the latter for scanning out the complete surface 12 of the member to be examined are unique for a given inspection operation. In other words, the type and dimensions of the transducer used, as well as the path taken by the latter, no matter whether they are imposed or of an arbitrary nature, determine the value of the signals supplied by the transducer.

However, in order to carry out an effective inspection of members, it is known that it is necessary to adapt the transducer and the path taken by it to the size and orientation of the defects. Thus, the orientation of a differential transducer is vital for the detection of point defects. Thus, at all times, such a transducer compares two adjacent zones of the examined member. Therefore the best perception of a defect is obtained when the differential signal supplied by the transducer is at a maximum, i.e. when the direction linking the two windings coincides with the largest variation gradient axis of the signal.

In the same way the size of the transducer must be of the same order of magnitude as that of the defects to be detected. Thus, if it is too large the transducer is only affected to a limited extent by the defect. However, if it is too small there is a risk of the transducer losing the perception of the defect because, on all sides, it "sees" only the defect.

However, there are at least two cases when these conditions cannot be realized during the scanning of the member by the transducer:

(1) When neither the size nor the orientation of the defects is known a priori.

(2) When the path taken by the transducer during a dynamic measurement is fixed.

Figure 1B:
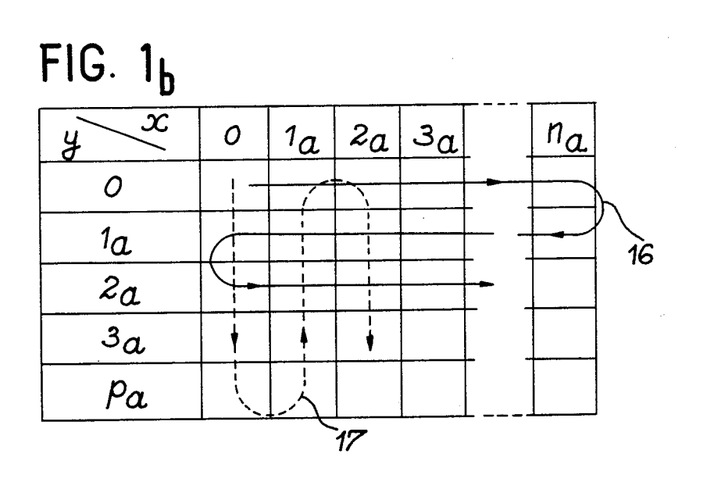

In order to obviate these disadvantages of the prior art, the principle of the process according to the invention consists, when scanning the surface 12 by transducer 14, subdividing said surface into a certain number of elementary measurement zones separated by an acquisition spacing a. In the case of a surface designated by two coordinates OX and OY, in the manner illustrated in FIG. 1a, said zones form a surface grid, whose fineness is dependent on the transducer size. This grid leads to the association with the examined surface 12 of a table of sampled values recorded during the displacement of transducer 14 with respect to the surface and in the manner illustrated in FIG. 1b. Thus, if transducer 14 moves along a path of the type designated by line 16 in FIG. 1a, the table of FIG. 1b is filled line by line in accordance with path 16. In other words the coordinates x and y of the transducer are associated with each box of the table of FIG. 1b and the sampled value of the signal supplied by it in this position, the filling direction of the boxes being imposed by path 16 followed by the transducer. According to the invention, the scanning of the surface of the member by the transducer is consequently accompanied by an acquisition of data constituted by the sampled values of the signal supplied by the transducer and recorded during the displacement of the latter.

Once the table of FIG. 1b has been filled, the dynamic notion of the filling direction disappears and is replaced by a static notion of values associated with positions x and y.

The rereading of the table of FIG. 1b at a clearly defined speed leads to the reappearance of a dynamic notion of the rereading direction simulating a simulated displacement of the transducer. Thus, this rereading is totally independent of path 16 followed by the transducer during data acquisition. Thus, the table of FIG. 1 can be reread both line by line and column by column (path 17 in FIG. 1b), or even obliquely from left to right, from bottom to top, top to bottom or in any other manner bringing the contiguous values end to end. Thus, it is possible to follow a path differing from path 16 and which is more favourable to the detection of certain defects.

The advantages offered by the filling of the table of FIG. 1b by means of sampled values of the signal supplied by the transducer 14 are not however limited to the possibility of rereading this table in accordance with a different path.

Thus, in the case shown in FIG. 1a, where the scanning of surface 12 has taken place by means of an absolute transducer having only one eddy current coil, it is possible at the time of rereading the table of FIG. 1b, to simulate a scan of surface 12 by means of a differential transducer, whose two windings are aligned on path 16 followed by transducer 14. Thus, the difference between the two contiguous values of the table of FIG. 1b corresponds to the differential measurement which could be carried out by a transducer, the two windings of which occupy the two positions in question.

In the not shown case, in which the transducer used during the surface scan is a differential transducer constituted in the simplest case by an eddy current probe having two coils, it is possible by carrying out a simulated displacement of the transducer, during the restoration of the signals, perpendicular to the true displacements of the transducer during the scan (line by line if scanning has taken place column by column or vice versa), to restore the signals corresponding to the simulated displacement of a simulated transducer, whose axis connecting the two windings is perpendicular to the axis connecting the two windings of the transducer used in the real surface scan.

Thus, if it is assumed that the table of FIG. 1b has been filled by means of a differential transducer, whose two windings are aligned with the displacement direction 16, the rereading of the table in a direction perpendicular to that of the filling simulates the displacement of a transducer, whose axis connecting the two windings is perpendicular to the displacement direction. The thus restored signals are applied in a pseudo-differential manner and, without having the characteristics of a true differential signal (in particular symmetry), they have a certain number of the characteristics thereof (immunity from drift and gaps).

In the opposite manner to the previous case, if data acquisition has taken place with an orientation of the windings orthogonal to the displacement direction, the table of FIG. 1b is filled by pseudo-differential measurements, but the signal reconstituted by placing the values end to end in a direction perpendicular to the filling will simulate a true differential measurement.

Another possibility offered by the rereading of the table of FIG. 1b consists of effecting, by simulation, an increase in the size or a modification of the shape of the transducer actually used during the scan. In this case, it is to be assumed that the table of FIG. 1b has been filled by means of a very small absolute transducer.

At the time of rereading the table, it is then possible to group a pluarlity of contiguous boxes of the table (e.g. four in the manner illustrated by lines $G_1$ in FIG. 2a) and calculate the mean value of the sampled values contained in these boxes in order to simulate the scanning of the member by means of a larger simulated absolute transducer.

Figure 2A:
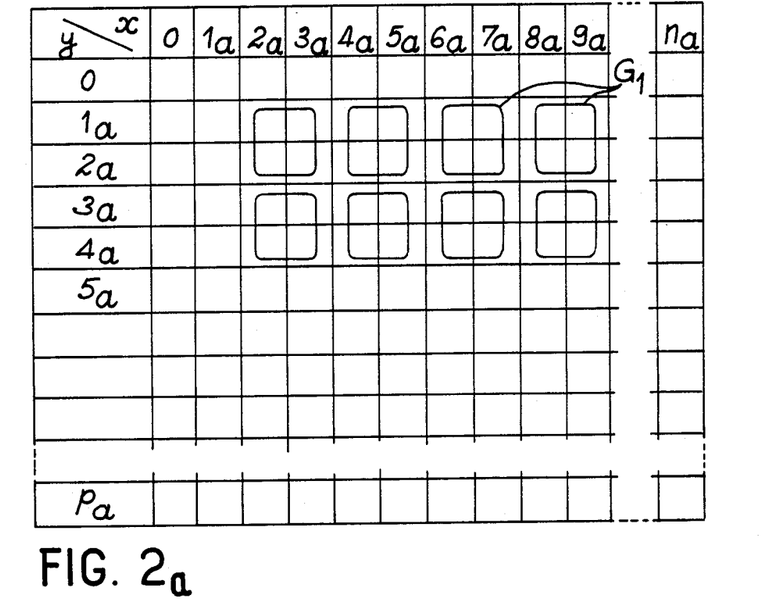
FIG. 2a is a table comparable to that of FIG. 1b illustrating the principle of an embodiment of the invention according to which, during the restoration of the signals, the signals are grouped into adjacent bodies of the table and the mean value is formed therefrom in order to simulate the surface scan by means of a larger transducer than that actually used.
Figure 2B:
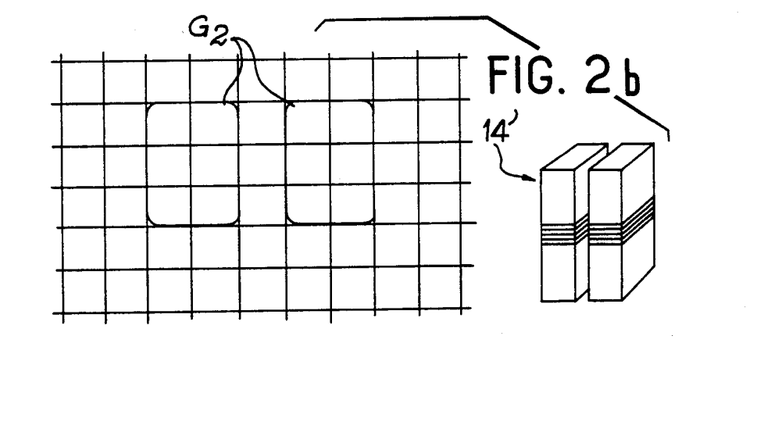
FIG. 2b is part of the table of FIG. 1b illustrating the principle of another embodiment of the invention according to which the signals are restored by grouping them in an appropriate manner so as to simulate the surface scan by means of a larger differential transducer, whereas the transducer used during the actual measurement was a smaller absolute transducer.

Moreover, and as illustrated in FIG. 2b, it is possible by forming the difference between the mean values of the sampled values contained in two adjacent groups of boxes $G_2$ which simulate an inspection by means of a simulated differential transducer 14' of the desired shape and adapted to the sought defect type.

A description will now be given, by means of examples, of three devices making it possible to perform the inspection process, whose principle has been described hereinbefore.

Figure 3:
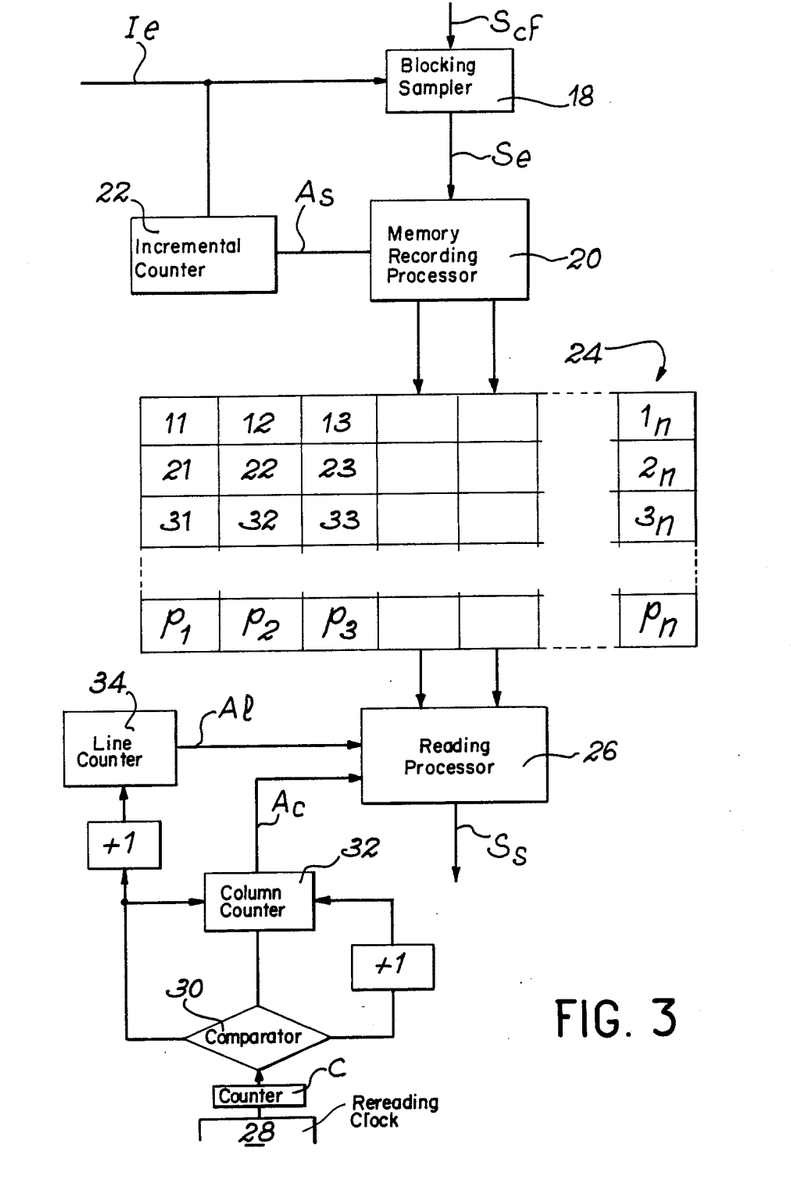
FIG. 3 diagrammatically illustrates a first embodiment of a device for performing the process according to the invention using stored signals supplied by the transducer and the subsequent restoration of these signals.

Thus, FIG. 3 diagrammatically illustrates an inspection device in which simulation is obtained by a digital processing of a data matrix. It can be seen that signal $S_{cf}$ from the eddy current means (not shown) is introduced into a blocking sampler 18, which receives a sampling pulse $I_e$ whenever the eddy current transducer moves by a value equal to the predetermined spacing a. Pulse $I_e$ can in particular be supplied by a not shown displacement transducer associated with the eddy current transducer.

For each sampling pulse $I_e$, the blocking sampler 18 supplies a sampled signal $S_e$ corresponding to the sampled value of signal $S_{cf}$ supplied at this time by the transducer. Each sampled signal $S_e$ enters a memory recording processor 20, which injects it into a memory 24, at the same time as the storage address $A_s$ corresponding thereto. The addressing of signals $S_e$ is carried out by means of an incremental counter 22 sensitive to the sampling pulses $I_e$ in order to associate in memory 24 a storage address $A_s$ with each of the sampled signals $S_e$. Thus, the table of FIG. 1b is restored in memory 24. Thus, if the breaking down of the inspected surface defines a table with n columns and p lines, memory 24 stores a matrix of n.p data. Each box of the matrix can, for example, be designated by a two-digit number, the first digit indicating the line and the second the column, in the manner illustrated in Fig.3.

The data stored in memory 24 is read by means of a reading processor 26, which is sensitive to a line address signal $A_1$ and to a column address signal $A_c$, in order to supply a series of output signals $S_s$ corresponding to the signals stored in the thus designated boxes.

In the represented variant, the matrix defined by memory 24 in reread column by column. To this end a rereading clock 28 transmits pulses to a counter C, whose output is applied to a comparator 30, which compares the content of counter C with the address p of the last line. When the content of C differs from p, a unit is added to a column counter 32, which supplies the column address signal $A_c$. However, when the content of C is equal to p, a unit is added to a line counter 34, which supplies the line address signal $A_l$. Simultaneously counter 32 is reset. Thus, on starting from box 1-1 of memory 24, processor 26 successively supplies the signals contained in boxes 2-1, 3-1 . . . P-1, 1-2, 2-2, 3-2, . . . P-2, . . . 1-n, 2-n, 3-n, . . . p-n.

Obviously the wired devices shown in FIG. 3 cannot be used when the recording of data can be limited in time (e.g. during the examination of a clearly defined area of a member, followed by a dead time, which can be used for carrying out a processing operation). Thus, this procedure runs up against the capacity limit of the memories. Thus, during continuous data acceptance, it is necessary to simultaneously process the matrix, so that the memory can be freed. The thus processed values can either be used for a graphic recording, as if they came directly from the eddy current means, or can be transmitted to another calculating unit, which carries out the desired processing operations on these simulated signals.

Figure 4:
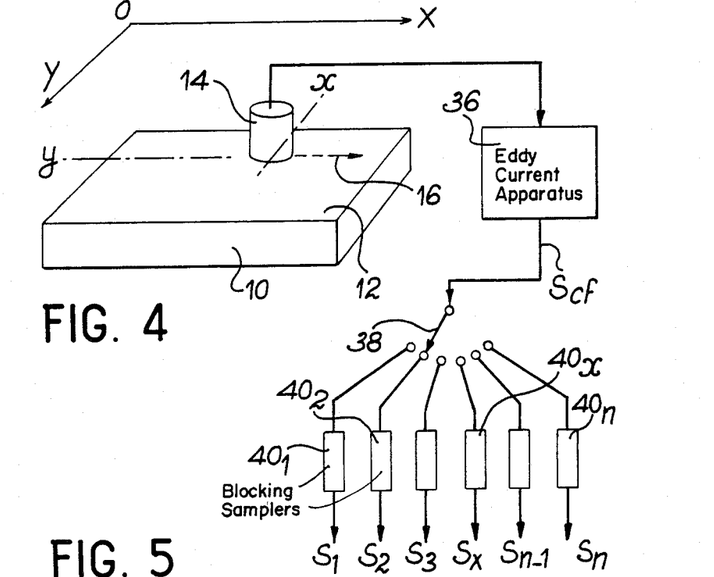
FIG. 4 diagrammatically shows a second embodiment of a device for performing the process according to the invention using real time branching of the signals supplied by the transducer.

FIG. 4 shows a second device for performing the process of the invention which, although having fewer possibilities than the aforementioned device, makes it possible to obviate any processing during continuous working and which is in fact very easy to use. Thus, in this device, the signals appear in real time, as if the simulated displacement had in fact taken place.

The second device is based on a simple principle. Instead of storing the sampled values in a memory having n.p points, they are directly supplied to an output providing the synthesized signal.

More specifically, it can be seen in FIG. 4 that the signal $S_{cf}$ supplied by the eddy current means 36, to which is connected transducer 14, is branched at 38 towards n channels numbered 1 to n. Each of these channels corresponds to one of the columns of the table of FIG. 1b, when transducer 14 moves line by line in the manner indicated by arrow 16 in FIG. 4. Each of the channels 1 to n is equipped with a blocking sampler $40_1$ to $40_n$, which supplies output signals $S_1$ to $S_n$, which are passed to n not shown recorders on which appear the variations of signals $S_1$ to $S_n$ as a function of time.

As stated hereinbefore with reference to FIG. 1a, the surface 12 of member 10 to be inspected is subdivided in direction OX into n columns and in direction OY into p. lines. Data acquisition takes place in direction OX, which is subdivided into n columns. When the transducer occupies abscissa position x, the sampled measurement is supplied to 38 and blocked at $40_x$ on the xth output of the device. When the transducer is in position x+1, the sampled signal is supplied to 38 and blocked at $40_{x+1}$ on the x+1 output, etc. When the transducer has described an ordinate line y, a value has been taken at each of the n outputs of the blocking samplers. The transducer continuing on the following line y+1 will supply the following value to each of the n outputs of the blocking samplers. Thus, for each line described, each output will receive the signal $S_x$, corresponding to the abscissa x which it represents. The measurements placed end to end at each of the outputs consequently simulate the n simultaneous displacements along direction OY, in the manner which they can be obtained by n transducers arranged side by side and moving in direction OY.

Figure 5:
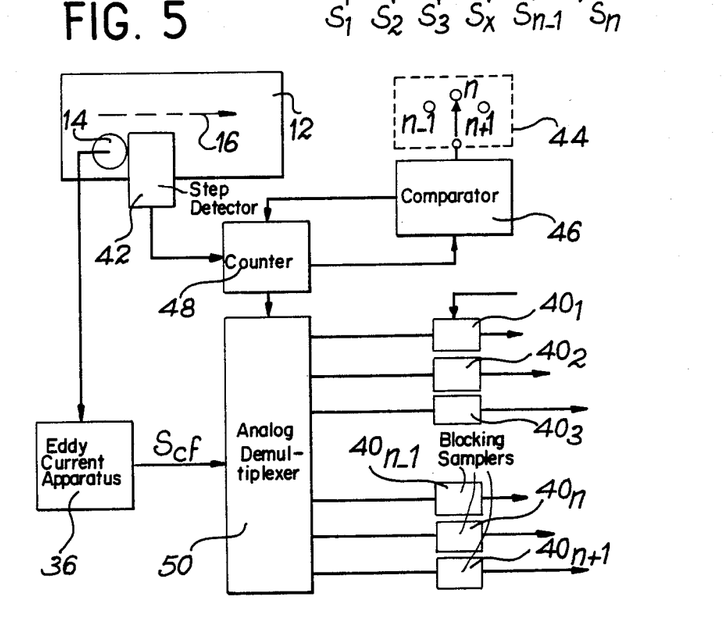
FIG. 5 diagrammatically shows a variant of the device of FIG. 4 making it possible to restore signals representing simulated displacements of the transducer in three different directions.

FIG. 5 is a variant of the device of FIG. 4, which also makes it possible to simulate two displacements by 45° and 135° with respect to the data acquisition direction. As in FIG. 4, the surface 12 of the member is broken down into n acquisition steps in the displacement direction corresponding to arrow 16, the support 42 of transducer 14 supplying a pulse for each step. The signal simulation system has in turn n+1 outputs numbered $S_1$ to $S_{n+1}$, which are not all used, as will be shown hereinafter.

This device differs from that of FIG. 4 particularly by the presence of a fictitious displacement selector which, as a function of the desired use, can be placed on values n−1, n or n+1. The value displayed on the selector is compared in a comparator 46 with the branching and sampling code constituted by the content of a counter 48 receiving the pulses supplied by the step detector 42 associated with transducer 14. The branching and sampling code is introduced at the same time as signal $S_{cf}$ supplied by the eddy current means 36 into an analog demultiplexer 50 supplying the different signals $S_{cf}$ successively to each of the channels leading to outputs 1 to n+1, to n or to n−1, as a function of selector 44, each of the channels having a blocking sampler $40_1$ to $40_{n+1}$, as in the case of the device of FIG. 4.

Figure 6A:
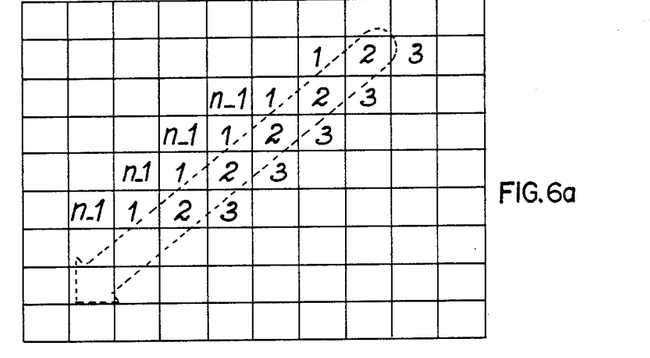
FIGS. 6a illustrate three displacements which can be obtained to 6c with the device of FIG. 5.
Figure 6B:
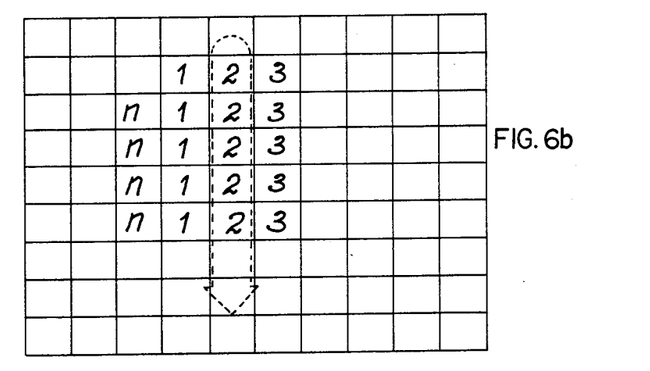

When selector 44 is placed on position n, the operation of the device of FIG. 5 is identical to that of FIG. 4, each of the n outputs used supplying a signal corresponding to a simulated displacement of the transducer orthogonal to its real displacement, in the manner illustrated in FIG. 6b.

When selector 44 is placed on position n−1, a hasty resetting of counter 48 branches the nth measurement to the first output and not to the nth output. It is therefore the second output, which receives the signal which should have returned to the first. This leads to the orientation of the simulated displacement counter to the real displacement because, for each line, there is an anticipation of data acceptance compared with the abscissa on the preceding line. FIG. 6a illustrates this situation simulating the oblique displacement of n−1 transducers, in which only n−1 outputs are used.

Figure 6C:
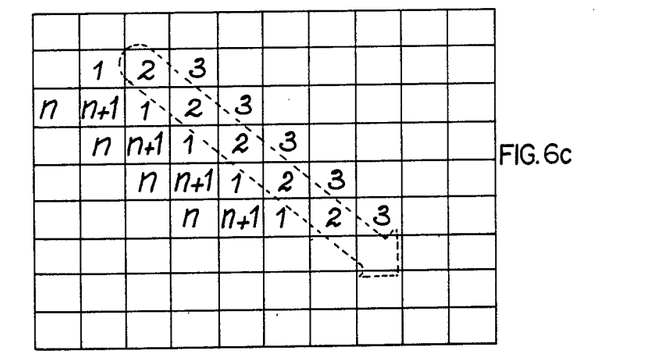

However, the selector positioned on n+1 introduces a delay in the return to the first output, whenever the transducer has described a line. This leads to a sliding of the values in the transducer displacement direction and consequently to an oblique simulated displacement in a direction orthogonal to the first direction. FIG. 6c illustrates this situation, in which the n+1 outputs are used.

When this process and these devices are used in investigating cracks in the tubes of steam generators equipping nuclear reactors, as well as in the examination of irradiated fuel rods equipping such reactors, it is readily apparent that it is possible to simulate the translation of a probe from the movement in accordance with a helix of given pitch. Numerous transducer displacement problems can be solved.

What is claimed is:

1. A device for inspecting the surface of a member by means of an eddy current transducer incorporating at least one eddy current probe and supplying a signal representing the state of said surface, wherein said device comprises means for scanning only the surface to be inspected by said transducer along a given path, means for sampling the values of said signal corresponding to elementary measurement zones of said surface separated by a given acquisition spacing, means for storing the sampled values of the signals supplied by the transducer, and means for restoring in a given order independent of said path and at a given speed a series of second signals, each of said second signals having a value deduced only from the sampled value(s) corresponding to at least one adjacent zone(s) of the surface, said series of second signals simulating an inspection of the surface which differs from the real scanning performed by said means for scanning only the surface.

2. A device for the inspection of the surface of a member by means of an eddy current transducer having at least one eddy current probe supplying a signal representing the state of said surface, wherein said device comprises means for scanning only the surface to be inspected by said transducer along a given path, means for sampling the values of said signal corresponding to elementary measurement zones of said surface separated by a given acquisition spacing along at least two different directions, means for supplying to different channels each of the sampled values of the signal supplied by the transducer for each of the elementary measurement zones along a first of said directions, and means for recording said sampled values on each of these channels, in accordance with an order corresponding to a second of said directions.

3. A process for inspecting a surface said process comprising the steps of
scanning only the surface to be inspected, along a given path, by an eddy current transducer comprising at least one eddy current probe supplying a signal representing the state of said surface;
sampling the values of the signal generated by the transducer corresponding to elementary measurement zones of said surface separated by a given acquisition spacing, thus obtaining a series of sampled values of the signal generated by the transducer;
recording said series of sampled values; and
restoring in a given order independent of the path and at a given speed a series of second signals, each of said signals having a value deduced only from the sampled value(s) corresponding to at least one adjacent zone(s) of the surface, said series of second signals simulating an inspection of the surface which differs from said step of scanning the surface.

4. A process according to claim 3 wherein an absolute transducer is used having at least one probe incorporating a single eddy current coil.

5. A process according to claim 3, wherein a differential transducer is used having at least one probe incorporating two eddy current coils.

6. A process according to claim 3, wherein each of said second signals has a value corresponding to one of the recorded sampled values, said given order of restoring differing from the path of scanning.

7. A process according to claim 6, wherein the zones define at least two directions, the scanning path following a first direction and the signal restoration order following a direction differing from that of the first direction.

8. A process according to claim 4, wherein each of said second signals represents the mean value of a group of sampled values corresponding to adjacent zones.

9. A process according to claim 4, wherein each of said signal represents the difference between the sampled values corresponding to two adjacent zones.

10. A process according to claim 4, wherein each of said second signals represents the difference between the mean values of two groups of sampled values corresponding to adjacent zones.

11. A process for inspecting a surface, said process comprising the steps of
scanning only the surface to be inspected, along a given path, by an eddy current transducer comprising at least one eddy current probe supplying a signal representing the state of said surface;
sampling the value of a signal generated by the transducer corresponding to elementary measurement zones of said surface separated by a given acquisition spacing;
recording the sampled values of the signal supplied by the transducer; and
restoring in a given order differing from the path and at a given speed a series of second signals, each of said second signals having a value equal to one of the recorded sampled values.

12. A process according to claim 11, wherein the zones define at least two directions, the scanning path following a first direction and the signal restoration order following a direction differing from that of the first direction.

13. A process for inspecting a surface said process comprising the steps of
scanning only the surface to be inspected, along a given path, by an eddy current absolute transducer comprising at least one eddy current probe incorporating a single eddy current coil supplying a signal respresenting the state of said surface;
sampling the value of a signal generated by the transducer corresponding to elementary measurement zones of said surface separated by a given acquisition spacing;
recording the sampled values of the signal supplied by the transducer; and
restoring in a given order independent of the path and at a given speed a series of second signals, each of said second signals having a value equal to the mean value of a group of sampled values corresponding to at least two adjacent zones of the surface.

14. A process for inspecting a surface said process comprising the steps of
scanning only the surface to be inspected, along a given path, by an eddy current absolute transducer comprising at least one eddy current probe incorporating a single eddy current coil supplying a signal respresenting the state of said surface;
sampling the value of a signal generated by the transducer corresponding to elementary measurement zones of said surface separated by a given acquisition spacing;
recording the sampled values of the signal supplied by the transducer; and
restoring in a given order independent of the path and at a given speed a series of second signals, each of said second signals having a value equal to the difference between the mean values of two groups of at least one value corresponding to adjacent zones of the surface.

* * * * *